United States Patent
Kraemer

(10) Patent No.: US 8,361,006 B2
(45) Date of Patent: Jan. 29, 2013

(54) BLOOD TREATMENT DEVICE

(75) Inventor: Matthias Kraemer, Bad Homburg (DE)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 0 days.

(21) Appl. No.: 12/801,086

(22) Filed: May 20, 2010

(65) Prior Publication Data

US 2011/0077575 A1   Mar. 31, 2011

Related U.S. Application Data

(63) Continuation of application No. 10/566,366, filed as application No. PCT/EP2004/008650 on Aug. 2, 2004, now abandoned.

(30) Foreign Application Priority Data

Aug. 25, 2003   (DE) .................................. 103 39 342

(51) Int. Cl.
    *A61M 37/00*   (2006.01)
(52) U.S. Cl. ....................................................... 604/6.09
(58) Field of Classification Search .............. 422/44–48; 604/4.01–6.16, 8–10; 210/739, 746, 85, 210/86, 97, 143
    See application file for complete search history.

(56) References Cited

U.S. PATENT DOCUMENTS

| | | | |
|---|---|---|---|
| 4,244,787 A | 1/1981 | Klein et al. | |
| 4,508,622 A | 4/1985 | Polaschegg et al. | |
| 5,100,554 A | 3/1992 | Polaschegg | |
| 5,744,031 A | 4/1998 | Bene et al. | |
| 6,126,831 A | 10/2000 | Goldau et al. | |
| 6,284,141 B1 * | 9/2001 | Shaldon et al. | 210/739 |
| 6,623,442 B2 | 9/2003 | Bene et al. | |
| 6,793,827 B1 * | 9/2004 | Bosetto et al. | 210/739 |
| 2003/0230533 A1 | 12/2003 | Gross et al. | |

FOREIGN PATENT DOCUMENTS

| | | |
|---|---|---|
| DE | 103 17 024 A1 | 4/2003 |
| DE | 102 12 247 C1 | 12/2003 |
| EP | 0 330 892 | 9/1989 |
| WO | WO 98/23311 | 6/1998 |
| WO | WO 01/32237 | 5/2001 |

OTHER PUBLICATIONS

Sargent, et al., "Principles and Biophysics of Dialysis", Replacement of Renal Function by Dialysis, 1996, pp. 34-102.
Knochel, "Clinical Expression of Potassium Disturbances", The Regulation of Potassium Balance, 1st Edition, 1989, pp. 207-240.
Lowrie, et al., "Death Risk in Hemodialysis Patients: The Predictive Value of Commonly Measured Variables and an Evaluation of Death Rate Differences Between Facilities", American Journal of Kidney Diseases, vol. XV, No. 5, pp. 458-482, May 1990.

* cited by examiner

*Primary Examiner* — Philip R Wiest
(74) *Attorney, Agent, or Firm* — Jacobson Holman PLLC

(57) ABSTRACT

A blood treatment device has a blood purification element divided into two chambers by a semipermeable membrane. With the device, nonphysiological conditions of the patient, in particular critical potassium concentrations and withdrawal rates, can be better prevented during the blood treatment. The device's analyzer unit determines on the basis of at least one sensor the concentration of a substance in the blood in the blood inlet line, the instantaneous transfer rate of this substance through the membrane, and the total quantity of this substance withdrawn during the treatment. The determined concentration is compared with a first admissible value range, the transfer rate is compared with a second admissible value range, and the quantity of the substance withdrawn is compared with a third value range. The device's control unit can instruct the device such that the blood treatment device performs the blood treatment while maintaining all three admissible value ranges.

12 Claims, 1 Drawing Sheet

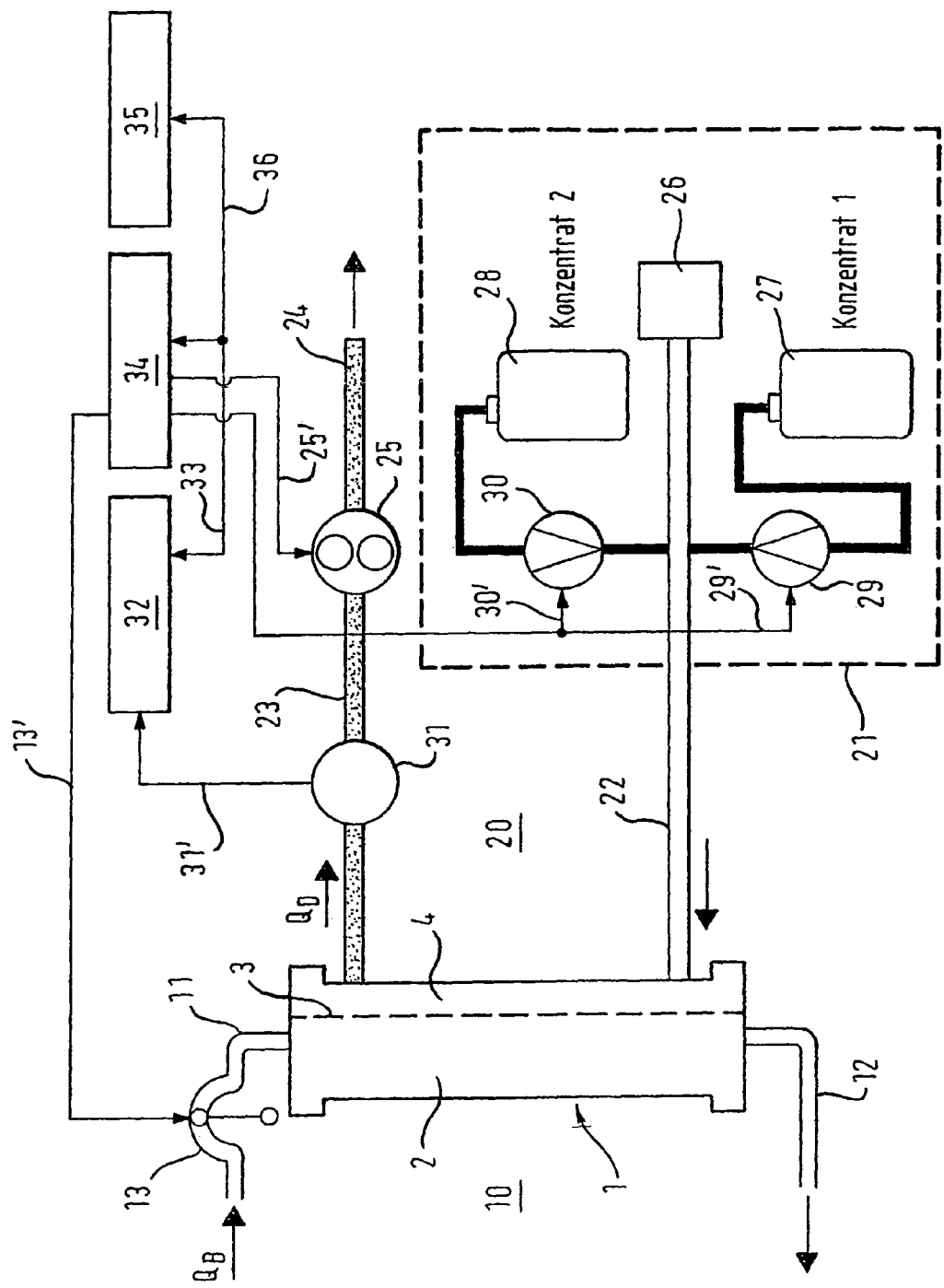

BLOOD TREATMENT DEVICE

CROSS-REFERENCE TO RELATED APPLICATIONS

This application is a continuation application of U.S. application Ser. No. 10/566,366, filed Jul. 10, 2006 now abandoned, the disclosure of which is incorporated by reference as if fully set forth herein, which is a nationalization of PCT/EP04/008650 filed Aug. 2, 2004, and published in German, and which claims priority to DE 103 39 342.0, filed Aug. 25, 2003.

BACKGROUND OF THE INVENTION

1. Field of Invention

This invention relates to the field of blood treatment devices having a blood purification element divided by a semipermeable membrane into two chambers, the first chamber being part of a dialysis fluid circuit and the second chamber being part of an extracorporeal blood circuit.

2. Description of the Prior Art

Such devices are used as hemodialysis machines in artificial kidney therapy. Through hemodialysis treatment, it is possible to withdraw excess water from a dialysis patient by means of a pressure gradient on a semipermeable membrane. On the other hand, substances such as urea and creatinine, which would otherwise be eliminated by healthy kidneys, are withdrawn from the patient according to a concentration gradient on the membrane. In the case of other substances—such as electrolytes—which are always present in blood in a certain concentration, concentrations corresponding to those in the blood of persons with healthy kidneys are usually used in the dialysis fluid.

Dialysis patients usually consume considerable quantities of potassium in their food intake between treatments. Excessive intake of potassium, in particular an accumulation over a long period of time The extracellular potassium concentration has an influence on the electrical resting membrane potential of cells. Therefore, this concentration influences the degree of electric stimulability of all stimulable cells (muscles, myocardium, nerves). The effect on cardiac electro-physiology in particular is important. Abnormal values can lead to life-threatening arrhythmias. Therefore, the body regulates the potassium concentration within narrow limits. Under the pathophysiological conditions of renal failure, dialysis therapy must be conducted in such a way as to prevent critical states.

Normal potassium concentrations are in the range of 3.5-4.5 mmol/L. Hyperkalemia is the condition when levels exceed 5.5 mmol/L; consequences include ventricular arrhythmia, ventricular fibrillations or even cardiac arrest. If the potassium level is below 2.5 mmol/L, this is called severe hypokalemia. Symptoms here include muscular weakness, atrial and ventricular arrhythmia, states of confusion and disorientation. The transitional ranges of mild hyperkalemia (4.5-5.5 mmol/L) and mild hypokalemia (2.5-3.5 mmol/L) are often largely symptom-free.

The potassium concentration is subject to much more complex kinetics during dialysis than the urea concentration, for example. Although urea is present in approximately the same concentrations intracellularly and extracellularly, the total potassium concentration of approximately 3500 mmol (50 mmol/kg) has a very irregular distribution: approx. 98% is intracellular and only 2% is extracellular. This imbalance between intracellular and extracellular concentrations is also influenced by changes in the concentration of other extracellular molecules, in particular $H^+$ ions, bicarbonate, glucose and insulin. Adrenergic stimulation and the aldosterone level also influence the concentration ratio. In addition, a strong rebound effect is observed, i.e., after the end of dialysis, the blood potassium concentration rises again considerably because of the time lag in the transfer from the intracellular space to the extracellular space.

Removal of approximately 90% of the quantity of potassium ingested since the previous treatment by intermittent dialysis is not always simple. Only a relatively low concentration gradient can be utilized. Initial potassium concentrations in dialysis patients are usually between approx. 3.6 and 7 mmol/L or in some cases even higher. The potassium concentration in the dialysis fluid is between 0 and 4 mmol/L, average concentrations of approx. 2 mmol/L being used in most cases. The usable gradients between blood and dialysis fluid therefore typically amount to 2-4 mmol/L at the start of dialysis, but are rapidly reduced during the treatment. Therefore, the total possible elimination of potassium is limited. If a larger quantity of potassium is ingested, there is also the risk that the total elimination may be too low. Therefore, patients are at risk of hyperkalemia, and this may be especially pronounced, in particular immediately before a dialysis treatment.

Using dialysis fluid having a low potassium concentration or even no potassium at all is not without risk. The potassium concentration may drop to a critically low level during dialysis, i.e., severe hypokalemia may be triggered (even if the total potassium level in the body is still adequate or even too high).

If the rate of potassium elimination is too high, it may lead to arrhythmia (J. P. Knochel: "Clinical Expression of Potassium Disturbances," in *The Regulation of Potassium Balance*, $1^{st}$ edition, edited by D. W. Seldin, G. Giebisch, 1989, pp. 207-240; E. G. Lowrie and N. L. Lew: "Death Risk in Hemodialysis Patients: The Predictive Value of Commonly Measured Variables and an Evaluation of Death Rate Differences Between Facilities," *American Journal of Kidney Disease* 15, pp. 458-482 (1990)). If there is an increase in the rate of elimination, the ratio of intracellular to extracellular potassium concentrations becomes greater, which then results in hyperpolarization of cells and thus a decline in stimulability. Therefore, there could be an increase in the probability of arrhythmia.

Administration of large quantities of bicarbonate to the patient, in particular in the early phase of dialysis, causes a shift in potassium from the extracellular space to the intracellular space, which also contributes to a reduction in the extracellular concentration and thus increases the risk of hypokalemia (in addition to the contribution made by the elimination of potassium via the dialysis machine).

There have been proposals for using model simulation with dialysis treatments to permit conclusions to be drawn regarding the removal of certain constituents of blood, in which case the calculations are supplemented by blood samples (S. Stiller, H. Mann and F. Raab, "Microprocessor-based universal dialysis calculator for individualization of artificial kidney dialysis," *MEDINFO* '80, edited by Lindberg/Kaihara, North-Holland Publishing Company, 1980, pp. 534-538).

U.S. Pat. No. 4,244,787 describes a device in which the concentration of a substance in the blood inlet line can be determined by a sensor in the dialysis fluid outlet line. At the same time, it is possible to determine the total quantity of the substance removed.

U.S. Pat. No. 4,508,622 describes a hemodialysis machine in which the electrolyte balance during a dialysis treatment can be determined by a sensor in the dialysis fluid discharge line and a similar sensor in the dialysis fluid inlet line, and feedback to the dialysis treatment is made possible. A similar machine is disclosed in European Patent EP 0 330 892 A2.

SUMMARY OF THE INVENTION

The object of this invention is to improve upon a blood treatment device having a blood purification element which is divided by a semipermeable membrane into two chambers, the first chamber of which is part of a dialysis fluid circuit and the second of which is part of an extracorporeal blood circuit. The improvement is to consist of providing a better means of preventing nonphysiological states of the patient during the blood treatment.

This object is achieved with a blood treatment device having the features described herein. Other advantageous embodiments of this invention are also described herein.

According to this invention, the analyzer unit of the blood treatment device determines on the basis of at least one sensor in a blood circuit or dialysis fluid circuit the concentration of a substance, which can penetrate through the semipermeable membrane and is present in the blood in the blood inlet line; this is done in order to determine the concentration of a substance which can permeate through the semipermeable membrane and to determine the instantaneous transfer rate of the substance through the membrane as well as the total quantity of this substance removed during the treatment; to compare the concentration with a first admissible value range and compare the amount of the substance eliminated with a third value range; and the control unit which controls the blood treatment device can send instructions to the blood treatment device so that it performs the blood treatment while maintaining all three admissible value ranges.

Such a device due to its inventive design allows critical substances such as potassium to be monitored and controlled within physiologically justifiable limits and periods of time during the blood treatment.

In an advantageous embodiment, the at least one sensor is situated in the dialysis fluid outlet line. If the concentration of the substance in question in the dialysis fluid inlet line is not known, another similar sensor may be provided there.

In the same way, it is also possible for such sensors to be provided in the blood circuit. However, because of the problems associated with contact with blood, sensors in the dialysis fluid circuit are generally preferable.

In a refinement of this invention, a target value within the third value range is stored in the analyzer unit, and the analyzer unit instructs the control unit so that the target value is reached at the end of the planned treatment period at the latest.

This invention can be used equally in a hemodialysis treatment or in a hemofiltration treatment. In the latter case, the dialysis fluid inlet line as the replacement fluid inlet line opens directly into the blood circuit, and the first chamber of the blood latter case, the dialysis fluid inlet line as the replacement fluid inlet line opens directly into the blood circuit, and the first chamber of the blood treatment machine is connected only to the dialysis fluid outlet line as the filtrate outlet line. Thus it is also possible in particular to use this machine in a combined treatment method, namely hemodiafiltration. For the sake of simplicity, however, the following discussion shall be devoted only to the components of a dialysis fluid circuit without interpreting this as being restricted to hemodialysis.

Additional details and advantages of this invention are described in greater detail below on the basis of an exemplary embodiment which is shown schematically in the drawing.

BRIEF DESCRIPTION OF THE DRAWINGS

The drawing FIGURE schematically illustrates an embodiment of a blood treatment device in accordance with the present invention.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The blood treatment device shown in the single FIGURE has an extracorporeal blood circuit 10 and a dialysis fluid circuit 20. In the blood circuit 10, blood is taken from a patient (not shown) and sent through a blood inlet line 11 to a second chamber 2 of a blood treatment element 1, which is divided by a semipermeable membrane 3 into two chambers 2 and 4. From the second chamber 2, the blood goes back to the patient through the blood return line 12. Blood is circulated in the extracorporeal blood circuit 10 by a blood pump 13.

In the dialysis fluid circuit 20, dialysis fluid goes from a dialysis fluid processing unit 21 through the dialysis fluid inlet line 22 to the first chamber 4 of fluid is circulated here with the dialysis fluid pump 25.

The dialysis fluid processing unit 21 prepares the dialysis fluid to be used according to specified mixing ratios using water or water already mixed with a few components of the dialysis fluid (connection 26) and a potassium concentrate 27 or to potassium concentrates 27 and 28 through concentrate pumps 29 and 30. It is possible to rely on proven components with which those skilled in the art are familiar but which need not be specified in detail here. Within the scope of this invention, it is essential only that the addition of the potassium concentrate to the dialysis fluid processing unit 21 can be adjusted in accordance with setpoint values.

A particularly advantageous implementation for providing dialysis fluid with an upper and a lower limit to the potassium concentration consists of working with two concentrates 27 and 28, whereby the first concentrate 27 has a low potassium concentration and the second concentrate 28 has a higher potassium concentration. If these concentrates also contain other substances, for example, the acidic components of the dialysis fluid and other electrolytes, then they are expediently present in both concentrates in equal concentration. Then at a constant rate of addition which is the sum of the concentrate flow pumped by the concentrate pumps 29 and 30, the potassium concentration can never go beyond a certain concentration range in the dialysis fluid.

A potassium-sensitive sensor 31 is provided in the dialysis fluid outlet line 23 and is connected by a line 31' to an analyzer unit 32. The analyzer unit 32 is in turn connected by a data line 33 to a control unit 34. The analyzer unit 32 and the control unit 34 may be designed as a single integrated unit. The control unit 34 is connected to the actuators and sensors of the blood treatment device to be able to perform the blood treatment as such in a controlled manner. To explain the present invention, these actuators and sensors include in particular the concentrate pumps 29 and 30 on the dialysis fluid pump 25 as well as the blood pump 13 which are connected by appropriate control lines 13', 25', 29' and 30' to the control line.

For the design of other components such as thermostatic units, monitoring units and balancing units, which are conventional in such a blood treatment machine, a variety of embodiments are known to those skilled in the art and therefore will not be discussed in greater detail here.

Now according to this invention, three admissible value ranges are stored in the analyzer unit 32 for the concentration CBI of potassium in the blood inlet line 11, for the transfer rate $\Delta M/\Delta t$ of potassium through the semipermeable membrane 3 and the total quantity M withdrawn.

For the first range, the minimum limit is preferably 2.5-3.5 mmol/L and the maximum limit is 4.5-5.5 mmol/L. It is also possible to provide a narrower first value range and an additional first value range which includes the former so that a milder form of hyperkalemia and hypokalemia and a more severe form of each can be counteracted in the form of two alarm levels.

For the second admissible value range, expediently a lower limit of 0 mmol/min is set because in general potassium is to be withdrawn from the patient. However, it is also possible to select a negative lower limit if it is suspected that the patient is already hypokalemic at the beginning of the treatment.

In the case of the third admissible value range, first a target value Mend for the total quantity of potassium to be withdrawn is stored in the analyzer unit 32. This target value can be input by an operating person via an interface (not shown in detail) or it may be set by the analyzer unit itself on the basis of reference data. In the simplest case, the third admissible value range is simply defined by a lower limit of 0 mol and by the upper limit Mend—i.e., the same as the target value.

The following processes take place in the blood treatment machine during the blood treatment.

The dialysis treatment is begun with a conventional composition of the dialysis fluid and conventional values for the blood flow Qb and the dialysis fluid flow Qd. After a measurement phase of a few minutes, at which point stable measured values have been established, the analyzer unit 32 obtains from the sensor 31 the concentration value Cdo of potassium in the dialysis fluid outlet line 25. In addition, the concentration Cdi of potassium in the dialysis fluid inlet line 22 is known to the analyzer unit 32 due to the predefined values of the control unit 34. To this end, a second similar sensor may also be provided in the dialysis fluid inlet line 22. The analyzer unit 32 determines with this information the blood concentration Cbi of potassium in the blood inlet line 11 using the following equation (J. A. Sargent and F. A. Gotch: "Principles and biophysics," in: Replacement of Renal Function by Dialysis, edited by C. Jacobs, et al., Kluwer Academic Publishers, Dordrecht, 1996, pp. 34ff):

$$Cbi = \frac{Qd(Cdo - Cdi)}{\alpha D} + \frac{Cdi}{\alpha}, \quad (1)$$

where D is the dialysance and $\alpha$ is the Gibbs-Donnan coefficient for potassium. The Gibbs-Donnan coefficient takes into account the ionic character of potassium for the transport properties through a semipermeable membrane, where $\alpha=1$ can be equated in first approximation. Otherwise another value determined accordingly is stored in the analyzer unit 32.

The dialysance D may have been previously entered into the analyzer unit by the user or it may have been measured initially by the blood treatment device using the known methods for this purpose. For example, the technique described in U.S. Pat. No. 5,100,554 may be used for this purpose. It is not necessary to determine the dialysance for potassium directly. It is sufficient to determine the dialysance for some other substance which has a fixed relationship to the dialysance for potassium, as is the subject of German Patent Application 10317024.3, to the disclosure content of which reference is herewith made explicitly.

Other methods, such as the method described in U.S. Pat. No. 6,126,831, for example, may also be used for the determination of Cbi.

For the sake of simplicity, the ultrafiltrate flow Qf, i.e., the net flow rate through the semipermeable membrane 3 from the second chamber 2 to the first chamber 4 has been equated with zero in equation (1). Those skilled in the art will be aware of modified equations, which take into account an ultrafiltration rate Qf that is not negligible. In this connection, reference is made explicitly to German Patent Application 10212247.4 by the present applicant for the application of this formalism to hemofiltration and hemodiafiltration.

After a brief initial measurement phase, the analyzer unit 32 compares the initial measured value of Cbi with the first admissible value range stored (in the unit). If the value is already outside the admissible value range, the analyzer unit 32 delivers an alarm signal via the control unit 34 and draws attention to the critical blood concentration via a display and input unit 35, which is connected to the control unit over a data line 36. The blood treatment is stopped automatically, so that the operating personnel can perform the additional steps.

If the measured value is within the first admissible range, the analyzer unit specifies, on the basis of the limits of the first and second admissible ranges and optionally the third admissible range, the additional treatment parameters so that the target value Mend for the total quantity of potassium to be withdrawn can be achieved as rapidly as possible within the third admissible value range without leaving all of the admissible value ranges. To do so, the dialysis fluid concentration is set at a value which is close to the lower limit of the first value range or at least at a distance from the instantaneous concentration value through a minimum difference. The dialysis fluid flow Qd or the blood flow Qb may optionally also be increased. In this way the dialysance and thus the transfer rate $\Delta M/\Delta t$ are also increased. The analyzer unit here may either proceed empirically or it may estimate the amount of time required for withdrawal of the quantity Mend on the basis of known equations for the dialysance of the concentrations and flows—as discovered in German Patent Application 10212247.4 so that it is possible to propose treatment parameters which permit complete withdrawal (of the substance) within the total treatment time T.

After this initial phase, the actual blood treatment begins. At regular intervals, the sensor 31 relays measured values to the analyzer unit 32 which determines the blood concentration Cbi(t) as described above and then also determines the transfer rate $\Delta M(t)/\Delta t$ and the total quantity of potassium withdrawn M(t) with the help of equations (2) and (3):

$$\frac{\Delta M(t)}{\Delta t} = Qd(t) \cdot (Cdo(t) - Cdi(t)), \quad (2)$$

$$M(t) = \int_0^t Qd(t') \cdot (Cdo(t') - Cdi(t')) \cdot dt', \quad (3)$$

The analyzer unit 32 compares all three values with the respective admissible value ranges. If there is the risk that the value will depart from the first or second range, then the analyzer unit 32 gives the control unit 34 appropriate instructions so that it is possible to counteract the tendency to leave the value ranges. For example, if the value for Cbi(t) is dropping too rapidly, the concentration of Cdi(t) can be increased accordingly. It is also possible to reduce the blood flow Qb(t) or the dialysis fluid flow Qd(t). The same thing is also true if the transfer rate $\Delta M(t)/\Delta t$ is too high.

On reaching the target value Mend=M(t), but at the latest on reaching the upper limit of the third value range—if these values differ from one another for some reason, the control unit 34 is instructed to set the potassium concentration Cdi(t) at a value corresponding to the blood value Cbi(t) so that by the end of the blood treatment there is no further withdrawal of potassium.

If the treatment time T has elapsed without being able to achieve the target quantity Mend despite the maximum transfer rate, this information is displayed to the user accordingly. To do so, the information may already be displayed for the user on entry of the treatment data because the maximum quantity of a substance to be removed during the treatment time T is obtained from the upper limit for the transfer rate multiplied by the treatment time T.

All the values calculated in the meantime are displayed for the operating person via the display and input unit 35. A wide variety of graphic aids may be used to display the individual values in relation to the admissible value ranges and any imminent departure of the value from the value ranges in a comprehensible manner. It is particularly advantageous to have an updated display directly after the initial determination of the potassium concentration because this value permits conclusions to be drawn regarding the tolerability of the treatment and a possible individualized adjustment of the individual value ranges. The analyzer unit 32 may also make recommendations regarding the individual value ranges on the basis of stored relationships with other patient-specific data such as height and weight.

The design of the blood treatment unit according to this invention prevents the blood concentration and the transfer rates of a substance passing through the semipermeable membrane of a blood treatment machine from going beyond physiological ranges, while at the same time a treatment in the sense of a quantity of a substance to be withdrawn is made possible with prioritized observance of the limits for the blood concentration and the transfer rate.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A blood treatment device comprising a blood purification element which is divided into two chambers by a semipermeable membrane, with a first chamber being part of a dialysis fluid circuit and a second chamber being part of an extracorporeal blood circuit,
    a dialysis fluid inlet line which leads from a dialysis fluid processing unit to supply fresh dialysis fluid to at least one of the first chamber and directly into the blood circuit,
    a dialysis fluid outlet line for removing spent dialysis fluid from the first chamber,
    a blood inlet line for supplying blood to the second chamber,
    a blood return line for returning blood from the second chamber,
    a control unit for controlling the blood treatment device,
    an analyzer unit which is connected to the control unit, and
    at least one sensor which is connected to the analyzer unit on at least one of the blood circuit and the dialysis fluid circuit for detecting the concentration of a substance which is capable of penetrating through the semipermeable membrane,
    the analyzer unit being configured (i) to determine on the basis of detected values of the at least one sensor the concentration Cbi of the substance in the blood in the blood inlet line, the instantaneous transfer rate $\Delta M/\Delta t$ of the substance through the membrane, and the total quantity M of the substance withdrawn through the membrane during the treatment, (ii) to store a first admissible value range for the blood concentration Cbi of the substance, a second admissible value range for the transfer rate $\Delta M/\Delta t$, and a third admissible value range for the total quantity M of the substance to be withdrawn, and (iii) to instruct the control unit such that the blood treatment device performs the blood treatment while maintaining all three of the admissible value ranges,
    the dialysis fluid processing unit being configured to add potassium to the fresh dialysis fluid, and
    the substance whose concentration is detected by the at least one sensor being potassium.

2. The blood treatment device according to claim 1, wherein the at least one sensor is provided in the dialysis fluid outlet line for determining a concentration Cdo.

3. The blood treatment device according to claim 2, wherein a second sensor is provided in the dialysis fluid inlet line for determining a concentration Cdi of the potassium and is connected to the analyzer unit.

4. The blood treatment device according to claim 2, wherein a concentration Cdi of the potassium in the dialysis fluid inlet line is predetermined by at least one of the control unit and the analyzer unit.

5. The blood treatment device according to claim 1, wherein the second value range extends from zero up to a maximum value.

6. The blood treatment device according to claim 1, wherein a target value Mend which is within the third value range is stored in the analyzer unit for the total quantity of the potassium to be withdrawn.

7. The blood treatment device according to claim 6, wherein the analyzer unit instructs the control unit that the target value Mend has been reached after a planned treatment time.

8. The blood treatment device according to claim 6, wherein the analyzer unit instructs the control unit that on reaching the target value Mend the blood treatment is to be continued with a concentration Cdi of the potassium in the dialysis fluid inlet line such that there is no longer any transfer of the potassium through the membrane.

9. The blood treatment device according to claim 1, wherein the control unit is configured for ordering an initial measurement of the blood concentration Cbi with preset treatment parameters and the analyzer unit is configured for determining an initial value of Cbi, and based on the initial value of Cbi, the first admissible value range and the second admissible value range for the blood treatment, proposing a value for at least one of a concentration Cdi of the potassium in the dialysis fluid inlet line, and a dialysis fluid flow Qd and a blood flow Qb.

10. The blood treatment device according to claim 9, wherein the analyzer unit determines the concentration Cdi based on the value which corresponds to a lower limit of the first admissible value range.

11. The blood treatment device according to claim 10, wherein a selection device for prioritizing the withdrawal of the potassium is provided on an input unit by an alignment with the lower limit of the first admissible value range or the upper limit of the second admissible value range.

12. The blood treatment device according to claim 9, wherein the analyzer unit determines the concentration Cdi by an upper limit of the second admissible value range.

* * * * *